United States Patent [19]

Lermer et al.

[11] Patent Number: 4,822,920
[45] Date of Patent: Apr. 18, 1989

[54] PREPARATION OF CYCLOPENTANONE

[75] Inventors: Helmut Lermer, Mannheim; Wolfgang Hoelderich, Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 116,879

[22] Filed: Nov. 5, 1987

[30] Foreign Application Priority Data

Nov. 7, 1986 [DE] Fed. Rep. of Germany ....... 3638005

[51] Int. Cl.$^4$ ............................................. C07C 45/48
[52] U.S. Cl. .................................................. 568/355
[58] Field of Search ........................................ 568/355

[56] References Cited

U.S. PATENT DOCUMENTS 2,863,923 12/1958 Bortnick ............................... 568/355
3,454,619 7/1969 Hayes .................................. 568/355

OTHER PUBLICATIONS

Houben-Weyl, Bd. VII/2a, p. 622.

Primary Examiner—James H. Reamer
Attorney, Agent, or Firm—Keil & Weinkauf

[57] ABSTRACT

Cyclopentanone is prepared from adipic esters by reacting adipic esters of the formula $$R^1OOC-(CH_2)_4-COOR^2$$

where $R^1$ and $R^2$ are alkyl of 1 to 12 carbon atoms, cycloalkyl of 5 or 6 carbon atoms, aralkyl or aryl and $R^2$ can additionally be hydrogen, in the gas or liquid phase at from 150° C. to 450° C. in the presence of zeolitic catalysts and/or phosphate catalysts, preferably zeolites of the pentasil type.

4 Claims, No Drawings

PREPARATION OF CYCLOPENTANONE

The present invention relates to a process for preparing cyclopentanone by reacting an adipic ester over a zeolitic catalyst or over a phosphate catalyst.

It is known to prepare cyclopentanone in the liquid phase by heating adipic acid in the presence of catalytic amounts of heavy metal salts. The metals used here are barium and thorium. Disadvantages of employing this process in industry are the corrosion problems which appear at the high temperatures and the use of toxic heavy metals.

We have found that cyclopentanone can be prepared in an advantageous manner by reacting an adipic ester of the formula

where $R^1$ and $R^2$ are each alkyl of 1 to 12 carbon atoms, cycloalkyl of 5 or 6 carbon atoms, aralkyl or aryl and $R^2$ can additionally be hydrogen, at from 150° C. to 450° C. in the presence of a zeolitic catalyst and/or in the presence of a phosphate catalyst.

The reaction according to the invention can be represented, for example for the conversion of dimethyl adipate to cyclopentanone, by the following equation:

$$H_3COOC-(CH_2)_4-COOCH_3 + H_2O \longrightarrow$$

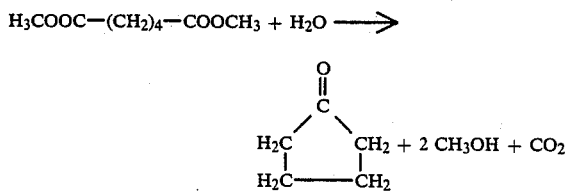

Prior art was to convert adipic esters into cyclopentanone via the intermediate methyl cyclopentanone 2-carboxylate by means of stoichiometric amounts of strong bases such as sodium alcoholates or sodium amides in a Dieckmann condensation. This process requires three steps. In addition, the base used needs to be neutralized, so that substantial amounts of neutral salts are inevitably produced.

The smooth catalytic conversion of an adipic ester to cyclopentanone is surprising. It was not foreseeable that this reaction over a zeolitic catalyst or a phosphate catalyst would proceed in one step and in high yield.

According to the invention, aliphatic, cycloaliphatic, araliphatic and aromatic mono- and diesters of adipic acid can be converted into cyclopentanone. Specific examples of $R^1$ and $R^2$ in (I) are: methyl, ethyl, propyl, isopropyl, butyl, isobutyl, tert.-butyl, hexyl, nonyl, dodecyl, cyclopentyl, cyclohexyl, phenyl and benzyl. Accordingly, it is possible to use the following adipic esters (I) as starting materials: dimethyl adipate, monomethyl adipate, diethyl adipate, dibutyl adipate, dicyclohexyl adipate and dibenzyl adipate.

Suitable catalysts for the purposes of the present invention are in general zeolites of the pentasil type, such as aluminosilicate zeolites, borosilicate zeolites or iron silicate zeolites, and zeolites of the faujasite type.

The zeolites may be doped for example with alkali metals, transition metals or rare earth metals.

Other suitable catalysts are phosphates of the elements B, Al, Zr, Fe, Sr and mixtures thereof. It is also possible to use hydrothermally prepared phosphates, for example hydrothermally prepared aluminum phosphates, silicon aluminum phosphates or silicon iron aluminum phosphates. The catalyst used can also be phosphoric acid on a carrier material.

The catalyst used for the process according to the invention is advantageously a zeolite in the acidic form. Zeolites are crystalline aluminosilicates which have a highly ordered structure comprising a rigid three-dimensional network of $SiO_4$ and $AlO_4$ tetrahedra linked by common oxygen atoms. The ratio of the Si and Al atoms:oxygen is 1:2. The electrovalence of the aluminum-containing tetrahedra is balanced by the inclusion in the crystal of cations, for example an alkali metal or hydrogen ion. Cation exchange is possible. The spaces between the tetrahedra are occupied by water molecules prior to dehydration through drying or calcination.

In the zeolites, the aluminum in the lattice can be replaced by other elements such as B, Ga, Fe, Cr, V, As, Sb, Bi or Be or mixtures thereof, or the silicon can be replaced by a tetravalent element such as Ge, Ti, Zr or Hf.

According to their structure, zeolites are divided into various groups. For instance, the zeolite structure is formed in the mordenite group by tetrahedra arranged in chains and in the chabasite group by tetrahedra arranged in layers, while in the faujasite group the tetrahedra form polyhedra, for example in the form of a cuboctahedron which is composed of tetragons and hexagons. Depending on the way the cuboctahedra are linked, which produces differently sized voids and pores, zeolites are classed as type A, L, X or Y.

Catalysts suitable for the process according to the invention are zeolites from the mordenite group or narrow-pored zeolites of the erionite or chabasite type or zeolites of the faujasite type, for example Y-, X- or L-zeolites.

This group of zeolites also includes the ultrastable zeolites of the faujasite type, i.e. dealuminized zeolites. Methods for preparing such zeolites have repeatedly been described.

Zeolites of the pentasil type are particularly advantageous. Their common feature is a pentagon composed of $SiO_4$ tetrahedra. They are characterized by a high $SiO_2/Al_2O_3$ ratio and by pore sizes between those of the zeolites of type A and those of type X or Y.

These zeolites can have different chemical compositions. They can be aluminosilicate, borosilicate or iron, beryllium, gallium, chromium, arsenic, antimony or bismuth silicate zeolites or mixtures thereof and aluminogermanate, borogermanate and gallium or iron germanate zeolites or mixtures thereof. Particularly suitable for the process according to the invention are the aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silicon dioxide in an aqueous amine solution, in particular in polyamines such as 1,6-hexanediamine or 1,3-propanediamine or triethylenetetramine solution, in the presence or in particular in the absence of alkali metal or alkaline earth metal at from 100° to 220° C. under autogenous pressure. This also includes the isotactic zeolites described in EP No. 34,727 and EP No. 46,504. The alumino-silicate zeolites obtained have an $SiO_2/Al_2O_3$ ratio of from 10 to 40,000, depending on the mixing ratio of the starting materials. These aluminosilicate zeolites of the pentasil type can also be synthesized in an ether medium such as diethylene glycol dimethyl ether, in an alcohol medium such as methanol or 1,4-butanediol, or in water.

The high-silicon zeolites usable according to the invention ($SiO_2/Al_2O_3 > 10$) also include the various ZSM types, ferrierite, Nu-1 and Silicalit ®.

Borosilicate zeolites can be synthesized under autogenous pressure, for example at from 90° to 200° C., by reacting a boron compound, for example $H_3BO_3$, with a silicon compound, preferably finely divided silicon dioxide, in an aqueous amine solution, in particular in 1,6-hexanediamine, 1,3-propanediamine or triethylenetetramine solution, in the presence or in particular in the absence of alkali metal or alkaline earth metal. They also include the isotactic zeolites described in EP No. 34,727 and EP No. 46,504. These borosilicate zeolites can also be prepared by carrying out the reaction not in aqueous amine solution but in an ether solution, for example diethylene glycol dimethyl ether, or in an alcohol solution, for example 1,6-hexanediol.

The iron silicate zeolite is obtained for example from an iron compound, preferably $Fe_2(SO_4)_3$, and a silicon compound, preferably finely divided silicon dioxide in an aqueous amine solution, in particular 1,6-hexanediamine, in the presence or absence of alkali metal or alkaline earth metal at from 100° to 200° C. under autogenous pressure.

The aluminosilicate, borosilicate and iron silicate zeolites thus prepared, after they have been isolated, dried at from 100° to 160° C., preferably at 110° C., and calcined at from 450° to 550° C., preferably at 500° C., can be combined with a binder in a ratio of from 90:10 to 40:60% by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C./16 h and calcined at 500° C./16 h.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silicoesters and graphite or mixtures thereof.

If the zeolite, on account of its manner of preparation, is present not in the catalytically active, acidic H-form but, for example, in the Na-form, it can be completely or partially converted into the desired H-form by ion exchange, for example with ammonium ions and subsequent calcination, or by treatment with acids.

Should the zeolitic catalyst used according to the invention undergo deactivation due to coking, it is advisable to regenerate the zeolite by burning off the coke deposit with air or with an air/$N_2$ mixture at from 400° to 550° C., preferably at 500° C. This restores the initial activity level of the zeolite.

By precoking it is possible to set the activity of the catalyst for optimum selectivity in respect of the desired reaction product.

To obtain a high selectivity, high conversions and long times on stream, it is advantageous to modify the zeolites. A suitable method of modifying the catalysts comprises for example doping the shaped or unshaped zeolite with metal salts by ion exchange or impregnation. The metals used are alkali metals such as Li, Cs or K, alkaline earth metals such as Mg, Ca or Sr, metals of main groups III, IV and V, such as Al, Ga, Ge, Sn, Pb or Bi, transition metals of subgroups IV-VIII, such as Ti, Zr, V, Nb, Cr, Mo, W, Mn, Re, Fe, Ru, Os, Co, Rh, Sr, Ni, Pd or Pt, transition metals of subgroups I and II, such as Cu, Ag or Zn, and rare earth metals such as La, Ce, Pr, Nd, Er, Yb or U.

Advantageously, doping is carried out by introducing the molded zeolite into a riser pipe and passing an aqueous or ammoniacal solution of a halide or nitrate of one of the abovementioned metals over it at from 20° to 100° C. Such an ion exchange can take place with the hydrogen, ammonium, or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least a drying step, and optionally by repeated calcination.

A possible embodiment comprises for example dissolving $Cu(NO_3)_2 \times 3\ H_2O$ or $Ni(NO_3)_2 \times 6\ H_2O$ or $Ce(NO_3)_3 \times 6\ H_2O$ or $La(NO_3)_2 \times 6\ H_2O$ or $Cs_2CO_3$ in water and impregnating the molded or unmolded zeolite with this solution for a certain period, for example 30 minutes. Any supernatant solution is stripped of water in a rotary evaporator. The impregnated zeolite is then dried at about 150° C. and calcined at about 550° C. This impregnating step can be carried out several times in succession until the desired metal content is obtained.

It is also possible to prepare an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous Ni($NO_3)_2$ solution or ammoniacal $Pd(NO_3)_2$ solution over it in a recycle loop and at a slightly elevated temperature of from 30° to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in molded or unmolded form, with an acid such as hydrochloric acid, hydrofluoric acid or phosphoric acid and/or steam, advantageously, for example, by treating the zeolite in pulverulent form with 1N phosphoric acid at 80° C. for 1 hour and then washing with water and drying at 110° C./16 h and calcining at 500° C./20 h. Alternatively, before or after being molded together with a binder, the zeolite is treated for example at from 60° to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400° C. to 500° C.

In a particular embodiment, the acid treatment comprises treating the zeolitic material, before it is molded, with hydrofluoric acid, generally in the form of 0.001N to 2 N, preferably 0.05 N to 0.5N, hydrofluoric acid, at an elevated temperature, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred form of the acid treatment, the zeolitic material, after it has been molded together with a binder, is treated at an elevated temperature, advantageously at from 50° to 90° C., preferably at from 60° to 80° C., for from 0.5 to 5 hours with, preferably, from 12 to 20% strength by weight hydrochloric acid. Expediently, the zeolitic material is subsequently washed, dried at from 100° to 160° C. and calcined at from 450° to 600° C. An HF treatment can also be followed by an HCl treatment.

Alternatively, zeolites can be modified by applying phosphorus compounds, such as trimethoxy phosphate, trimethoxyphosphine or primary, secondary or tertiary sodium phosphate. The treatment with primary sodium phosphate has proven to be particularly advantageous. In this treatment, the zeolite in the extrudate, tablet or fluidizable form is saturated with aqueous $NaH_2PO_4$ solution, and dried at 110° C. and calcined at 500° C.

Further catalysts for preparing cyclopentanone from an adipic ester are phosphates, in particular aluminum phosphates, silicon aluminum phosphates, iron aluminium phosphates, cerium phosphate, zirconium phosphates, boron phosphate, iron phosphate or mixtures thereof.

Suitable aluminum phosphate catalysts for the process according to the invention are in particular aluminum phosohates synthesized under hydrothermal conditions. Examples of suitable aluminum phosphates are APO-5, APO-9, APO-11, APO-12, APO-14, APO-21, APO-25, APO-31 and APO-33.

$AlPO_4$-5 (APO-5), for example, is synthesized by by homogeneously mixing orthophosphoric acid with pseudoboehmite (Catapal SB ®) in water, adding tetrapropylammonium hydroxide to this mixture, and then reacting in an autoclave under autogenous pressure at about 150° C. for from 20 to 60 hours. The $AlPO_4$ is filtered off, dried at from 100° to 160° C. and calcined at from 450° to 550° C.

$AlPO_4$-9 (APO-9) is likewise synthesized from orthophosphoric acid and pseudoboehmite, but in aqueous DABCO solution (1,4-diazabicyclo(2,2,2)octane) at about 200° C. under autogenous pressure in the course of from 200 to 400 hours. If ethylenediamine is used in place of DABCO solution, APO-12 is obtained.

The synthesis of $AlPO_4$-21 (APO-21) is effected from orthophosphoric acid and pseudoboehmite in aqueous pyrrolidine solution at from 150° to 200° C. under autogenous pressure in the course of foom 50 to 200 hours.

The process according to the invention can also be carried out with known silicon aluminum phosphates such as SAPO-5, SAPO-11, SAPO-31 and SAPO-34. These compounds are prepared by crystallization from aqueous mixture at from 100° to 250° C. and under autogenous pressure in the course of from 2 hours to 2 weeks, the reaction mixture, comprising a silicon, an aluminum and a phosphorus component, being converted in an aqueous amine-containing solution.

SAPO-5, for example, is obtained by mixing $SiO_2$, suspended in an aqueous tetrapropylammonium hydroxide solution, with an aqueous suspension of pseudoboehmite and orthophosphoric acid and then reacting at from 150° to 200° C. under autogenous pressure in a stirred autoclave for from 20 to 200 hours. The powder is filtered off, dried at from 110° to 160° C. and calcined at from 450° to 550° C.

Suitable silicon aluminum phosphates also include ZYT-5, ZYT-6, ZYT-7, ZYT-9, ZYT-11 and ZYT-12.

The phosphate catalyst used in the process can be a precipitated aluminum phosphate. For example, such an aluminum phosphate is prepared by dissolving 92 g of diammonium hydrogenphosphate in 700 ml of water. 260 g of $Al(NO_3)_3 \times 9\ H_2O$ in 700 ml of water are added dropwise to this solution in the course of 2 hours, during which pH 8 is maintained by adding 25% strength $NH_3$ solution at the same time. The resulting precipitate is subsequently stirred for 12 hours and then filtered off with suction and washed. It is dried at 60° C./16 h.

A boron phosphate catalyst for use in the process according to the invention can be prepared for example by mixing and kneading concentrated boric acid and phosphoric acid and subsequently drying and calcining in an inert gas, air or vapor atmosphere at from 250° to 650° C., preferably at from 300° to 500° C.

$CePO_4$ is obtained by precipitating 52 g of $Ce(NO_3)_3 \times 6\ H_2O$ and 56 g of $NaH_2PO_4 \times 2\ H_2O$. After filtration the material is molded into extrudates, which are dried at 120° C. and calcined at 450° C. Suitable phosphates for the process according to the invention also include $SrHPO_4$, $FePO_4$ and $Zr_3(PO_4)_4$.

The catalysts described here can optionally be used in the form of from 2 to 4 mm extrudates or as tablets from 3 to 5 mm in diameter or as chips having particle sizes of from 0.1 to pb 0.5 mm, or in a fluidizable form.

The reaction is preferably carried out in the gas phase at from 150° to 450° C., in particular at from 200° C. to 400° C., operating at a weight hourly space velocity (WHSV) of from 0.1 to 20 $h^{-1}$, preferably from 0.5 to 5 $h^{-1}$ (g of feed mixture per g of catalyst per hour). It is also possible to carry out the reaction in the liquid phase (by the suspension, trickle bed or liquid phase procedure) at from 50° to 200° C.

The process is generally carried out under atmospheric pressure or, depending on the volatility of the starting compound, under reduced or superatmospheric pressure, and preferably continuously. Involatile or solid starting materials are used in dissolved form, for example in solution in THF, toluene or petroleum ether. In general, the starting material can be diluted with such a solvent or with an inert gas such as $N_2$, or Ar or with $H_2O$ vapor.

In a preferred embodiment of the process according to the invention in the gas phase, for example, a mixture of an adipic ester (I) and water is initially vaporized and then passed, with or without an inert gas, such as nitrogen or argon, in gas form at the desired reaction temperature into a fluidized catalyst bed. The output from the reaction is condensed by means of a suitable cooler and then worked up by fractional distillation. Unconverted adipic ester can be recycled.

The adipic ester (I) required as a starting material can be prepared by esterifying adipic acid in a conventional manner or starting from butadiene by double carbonylation in the presence of an alcohol.

Cyclopentanone is a useful intermediate. For instance, reductive amination gives cyclopentylamine which is required for the synthesis of crop protection agents and pharmaceuticals.

EXAMPLES 1 to 9

The reaction is carried out under isothermal conditions in the gas phase in a tubular reactor (helix, internal diameter 0.6 cm, length 90 cm). The gaseous reaction outputs are condensed, weighed and analyzed by gas chromatography in a conventional manner.

The catalysts used in each case are:

Catalyst A

An aluminum silicate zeolite of the pentasil type is prepared under hydrothermal conditions and autogenous pressure and at 150° C. in a stirred autoclave from 650 g of finely divided $SiO_2$ and 203 g of $Al_2(SO_4)_3 \times 18$ $H_2O$ in 10 kg of an aqueous 1,6-diaminohexane solution (mixture: 50:50% by weight). After filtering and washing, the crystalline reaction product is dried at 110° C./24 h and calcined at 500° C./h. This aluminosilicate zeolite contains 92.8% by weight of $SiO_2$ and 4.2% by weight of $Al_2O_3$. This material is molded with a molding aid in 2 mm extrudates which are dried at 110° C./16 h and calcined at 500° C./24 h.

Catalyst B

An iron silicate zeolite of the pentasil type is prepared under hydrothermal conditions and autogenous pressure at 165° C. in a stirred autoclave from 273 g of sodium silicate (27.2% of $SiO_2$, 8.5% of $Na_2O$), 126 g of 1,6-diaminohexane, 551 g of water, 20.6 g of 96% strength sulfuric acid and 31.1 g of iron(III) sulfate. After filtering and washing, the crystallized reaction product is dried at 110° C./24 h and calcined at 500° C./24 h. This iron silicate zeolite has an $SiO_2/Fe_2O_3$ ratio of 17.7 and a $Na_2O$ content of 1.2% by weight. This material is molded with pyrogenic silica (8 parts weight:2 parts weight) and a molding aid into 2 mm extrudates which are dried at 110° C./16 h and calcined at 500° C./24 h.

Catalyst C

A borosilicate zeolite of the pentasil type is prepared in a hydrothermal synthesis at autogenous pressure and 170° C. in a stirred autoclave from 640 g of finely divided $SiO_2$, 122 g of $H_3BO_3$ and 8,000 g of an aqueous 1,6-diaminohexane solution (mixture 50:50% by weight). After filtering and washing, the crystalline reaction product is dried at 100° C./24 h and calcined at 500° C./24 h. This borosilicate zeolite comprises 94.2% by weight of $SiO_2$ and 2.3% by weight of $B_2O_3$.

This material is molded with a molding aid to 2 mm extrudates which are dried at 110° C./16 h and calcined at 500° C./24 h.

The extrudates are exchanged with an aqueous $Zn(NO_3)_2$ solution, dried at 110° C./16 h and calcined at 500° C./16 h. The Zn content is 0.58% by weight.

Catalyst D

Catalyst D is prepared in the same way as catalyst C by ion exchange of the borosilicate zeolite extrudates with an aqueous $Co(NO_3)_2$ solution, subsequent drying at 110° C./16 h and calcination at 500° C./16 h. The Co content is 0.3% by weight.

Catalyst E

Catalyst E is prepared by impregnating the borosilicate zeolite extrudates with aqueous $Co(NO_3)_2$ solution, subsequent drying at 110° C./16 h and calcination at 500° C./16 h. The Co content is 0.9% by weight.

Catalyst F

Catalyst F is an aluminum phosphate precipitated at pH 8 (42% by weight of $Al_2O_3$, 58% by weight of $P_2O_5$). The powder is molded after addition of 20% of potassium propionate into 2 mm extrudates which are dried at 110° C./16 h and calcined at 550° C./1.5 h.

Catalyst G

Catalyst G is prepared by ion exchange on the extrudates of catalyst B with an aqueous $Co(NO_3)_2$ solution, subsequent drying at 110° C./16 h and calcination at 500° C./16 h. The Co content is 0.57% by weight and the Na content 0.10% by weight.

Table 1 shows the results obtained with these catalysts after a run of 4 h in each case.

TABLE 1

Catalyst test in synthesis of cyclopentanone from DMA (dimethyl adipate)

| Examples | Catalyst | Temperature [°C.] | WHSV [h$^{-1}$] | Weight ratio DMA:THF | Conversion DMA [%] | Selectivity cyclopentanone | Yield [%] |
|---|---|---|---|---|---|---|---|
| 1 | A | 400 | 3.7 | 1.0 | 42.6 | 38.5 | 16.4 |
| 2 | B | 350 | 2.7 | 1.0 | 34.1 | 87.8 | 29.9 |
| 3 | B | 400 | 3.2 | 1.0 | 86.5 | 58.2 | 50.4 |
| 4 | B | 450 | 2.4 | 1.0 | 97.8 | 23.7 | 23.2 |
| 5 | C | 400 | 2.6 | 1.0 | 68.3 | 57.8 | 39.5 |
| 6 | D | 400 | 3.1 | — | 29.5 | 43.5 | 12.8 |
| 7 | D | 400 | 2.8 | 1.0 | 41.6 | 73.9 | 30.7 |
| 8 | E | 400 | 3.5 | 1.0 | 56.0 | 59.6 | 33.4 |
| 9 | F | 400 | 2.6 | 1.0 | 75.3 | 57.2 | 43.1 |

EXAMPLE 10

46.2 g of dimethyl adipate per hour and an equimolar amount of water are vaporized at 350° C. and passed at 350° C. with a nitrogen stream of 15 l/h over 50 g of catalyst B. The output from the reaction is condensed, weighed and analyzed by gas chromatography in a conventional manner.

| Duration of run [h] | Conversion DMA [%] | Selectivity cyclopentanone [%] |
|---|---|---|
| 24 | 87.4 | 88.3 |
| 48 | 81.0 | 99.1 |

EXAMPLE 11

20.4 g of dimethyl adipate per hour and water in a molar ratio of 1:2 (dimethyl adipate:water) are vaporized at 353° C. and passed at 353° C. over 50 g of catalyst G. The output from the reaction is condensed, weighed and analyzed by gas chromatography in a conventional manner. The catalyst was kept on stream for 216 hours. The conversion during the period under observation was within the range from 99.5 to 100%, and the selectivity for cyclopentanone within the range from 75 to 79%. During this time on stream there was no noticeable deactivation of the catalyst.

We claim:

1. A process for preparing cyclopentanone from an adipic ester, which comprises reacting an adipic ester of the formula $$R^1OOC-(CH_2)_4COOR^2 \qquad (I)$$

where $R^1$ and $R^2$ are each alkyl of 1 to 12 carbon atoms, cycloalkyl of 5 or 6 carbon atoms, aralkyl or aryl and $R^2$ can additionally be hydrogen, in the gas or liquid phase at from 150° C. to 450° C. in the presence of a zeolight catalyst having a pentasil or faujasite structure and/or of a phosphate catalyst containing the $PO_4^{3-}$ ion.

2. The process of claim 1, wherein the catalyst used is a zeolite of the pentasil type.

3. The process of claim 1, wherein the catalyst used is an aluminum phosphate, a silicon aluminum phosphate, an iron aluminum phosphate, a boron phosphate, a cerium phosphate or a zirconium phosphate.

4. The process of claim 3, wherein the catalyst used is a hydrothermally prepared phosphate having a zeolite-like structure.

* * * * *